US 8,138,301 B2

(12) United States Patent
Newkome et al.

(10) Patent No.: US 8,138,301 B2
(45) Date of Patent: Mar. 20, 2012

(54) CONVENIENT SYNTHESIS OF 1→3 C-BRANCHED DENDRONS

(75) Inventors: George R. Newkome, Medina, OH (US); Charles N. Moorefield, Akron, OH (US); Kishore K. Kotta, Akron, OH (US)

(73) Assignee: The University of Akron, Akron, OH (US)

( * ) Notice: Subject to any disclaimer, the term of this patent is extended or adjusted under 35 U.S.C. 154(b) by 679 days.

(21) Appl. No.: 11/719,113

(22) PCT Filed: Nov. 11, 2005

(86) PCT No.: PCT/IB2005/053729
§ 371 (c)(1),
(2), (4) Date: Oct. 26, 2009

(87) PCT Pub. No.: WO2006/051506
PCT Pub. Date: May 18, 2006

(65) Prior Publication Data
US 2010/0041859 A1    Feb. 18, 2010

Related U.S. Application Data

(60) Provisional application No. 60/626,956, filed on Nov. 11, 2004.

(51) Int. Cl.
*C08G 69/10*   (2006.01)
(52) U.S. Cl. ........ 528/332; 525/410; 525/419; 528/271; 528/310; 528/350; 528/363; 528/373
(58) Field of Classification Search ............... 528/332, 528/310, 350, 363, 373; 525/410
See application file for complete search history.

(56) References Cited

U.S. PATENT DOCUMENTS

| 4,694,064 A | 9/1987 | Tomalia et al. |
| 5,703,271 A | 12/1997 | Newkome et al. |

OTHER PUBLICATIONS

Newkome, G.R.; Moorefield, C.N.; Vogtle, F. In Dendrimer and Dendrons: Concepts, Syntheses, Applications; Wiley-VCH: Weinheim, Germany, 2001.
Newkome, G.R.; Behera, R.K.; Moorefield, C.N.;Baker, G.R. J. Org. Chem. 1991, 56, 7162-7167.
Newkome, G.R.; Nayak, A.; Behera, R.K.; Moorefield, C.N.; Baker, G.R. J. Org. Chem. 1992, 57, 358-362.
Newkome, G.R.; Weis, C.D. Org. Prep. Proced. Int. 1996, 28, 485-488.
Newkome, G.R.; Weis, C.D.; Moorefield, C.N.; Fronczek, F.R. Tetrahedron Lett. 1997, 38, 7053-7056.
Newkome, G.R.; Weis, C.D.; Moorefield, C.N.; Baker, G.R.; Childs, B.J.; Epperson, J.D. Angew. Chem. Int. Ed. 1998, 37, 307-310.
Brettreich, M.; Hirsch, A. Synlett 1998, 1396-1398.
Brettreich, M.; Hirsch, A. Tetrahedron Lett. 1998, 39, 2731-2734.
Brettreich, M.; Burghardt, S.; Bottcher, C.; Bayerl, T.; Bayerl, S.; Hirsch, A. Angew. Chem. Int. Ed. 2000, 39, 1845-1848.
Texier, I.; Berberan-Santos, M.; Fedorov, A.; Brettreich, M.; Schonberger, H.; Hirsch, A.; Leach, S.; Bensasson, R.V. J. Phys. Chem. A. 2001, 105, 10278-10285.
Braun, M.; Atalick, S.; Guldi, D.M.; Lanig, H.; Brettreich, M.; Burghardt, S.; Hatzimarinaki, M.; Ravanelli, E.; Prato, M.; van Eldik, R.; Hirsch, A. Chem. Eur. J. 2003, 9, 3867-3875.
Zilbermann, L; Lin, A.; Hatzimarinaki, M.; Hirsch, A.; Guldi, D.M. Chem. Commun. 2004, 96-97.
Hao, J.; Li, H.; Liu, W.; Hirsch, A. Chem. Commun. 2004, 602-603.
Guldi, D.M.; Zilbermann, I.; Anderson, G.; Li, A.; Balbinot, D.; Jux, N.; Hatzimarinaki, M.; Hirsch, A.; Prato, M. Chem. Commun. 2004, 726-727.
Braun, M.; Hartnagel, U.; Ravanelli, E.; Schade, B.; Bottcher, C.; Vostrowsky, O.; Hirsch, a. Eur. J. Org. Chem. 2004, 1983-2001.
Kellermann, M.; Bauer, W.; Hirsch, A.; Schade, B.; Ludwig, K.; Bottcher, C. Angew, Chem. Int. Ed. 2004, 43, 2959-2962.
Cardona, C.M.; Kaifer, A.E. J. Am. Chem. Soc. 1998, 120, 4023-4024.
Cardona, C.M.; Alvarez, J.; Kaifer, A.E.; McCarley, T.D.; Pandey, S.; Baker, G. A.; Bonzagni, N.J.; Bright, FIV. J. Am. Chem. Soc. 2000, 122, 6139-6144.
Cardona, C.M.; McCarley, T.D.; Kaifer, A.E. J. Org. Chem. 2000, 65, 1857-1864.
Cardona, C.M.; Mendoza, S.; Kaifer, A.E. Chem. Soc. Rev. 2000, 29, 37-42.
Cardona, C.M.; Wiles, T.; Ong, W.; Kaifer, A.E.; McCarley, T.D.; Pandey, S.; Baker, G.A.; Kane, M.N.; Baker, S.N.; Bright, F.V. J. Phys. Chem. B. 2002, 106, 8649-8656.
Collman, J.P.; Fu, L.. Acc. Chem. Res. 1999, 32, 455-463.
Joester, D.; Losson, M.; Pugin, R.; Heinzelmann, H.; Walter, E.; Merkle, H.P.; Diederich, F. Angew. Chem. Int. Ed. 2003, 42, 1486-1490.
Kimura, M.; Sugihara, Y.; Muto, T.; Hanabusa, K.; Shirai, H.; Kobayashi, N. Chem. Eur. J. 1999, 5, 3495-3500.
Narayanan, V.V.; Wiener, E.C. Macromolecules 2000, 33, 3944-3946.
Ong, W.; Kaifer, A.E. J. Am. Chem. Soc. 2002, 124, 9358-9359.
Pandy, S.; Redden, R.A.; Fletcher, K.A.; Sasahi, D.Y.; Kaifer, A.E. Chem. Commun. 2004, 1318-1319.
Wang, Y.; Cardona, C.M.; Kaifer, A.E. J. Am. Chem. Soc. 1999, 121, 9756-9757.
Weyermann, P.; Diederich, F. Chimia 1999, 53, No. 202.
Dominguez, X.A.; Lopez, I.C.; Franco, R. J. Org. Chem. 1961, 26, 1625.

*Primary Examiner* — James J Seidleck
*Assistant Examiner* — Gregory Listvoyb
(74) *Attorney, Agent, or Firm* — Renner Kenner Greive Bobak Taylor & Weber

(57) ABSTRACT

In accordance with the present invention, there is provided a method of preparing higher generation 1→3 C-branched polyamide dendrons. The combination of commercially available acryloyl chloride with 1→3 C-branched amines, e.g., di-tert-butyl 4-[2-(tert-butoxycarbonyl)ethyl]-4-aminoheptanedioate, resulted in generally high yields of acryl amides, which upon treatment with other reagents, generated the desired higher generation dendrons. These second and third generation dendrons were fully characterized and compared to the samples prepared from a convergent synthesis.

7 Claims, 3 Drawing Sheets

CONVENIENT SYNTHESIS OF 1→3 C-BRANCHED DENDRONS

This application claims the benefit of U.S. Provisional Patent Application Ser. No. 60/626,956, filed Nov. 11, 2004, herein incorporated by reference.

FIELD OF THE INVENTION

The present invention relates to highly branched molecules possessing a predetermined three-dimensional morphology. More specifically, the present invention relates to the preparation of second and third generation polyamide dendrons.

BACKGROUND OF THE INVENTION

Dendrons are used as versatile building blocks in organic chemistry in order to design stereochemically defined macromolecules or polymers with desired solubility, polarity, amphiphilic, molecular aggregation, biological activity, reactivity, catalytical, and photochemical properties. Among the various types of dendritic building blocks, the 1→3 C-branched polyamide dendrimers are of interest due to their high branching multiplicity and bulkiness as well as the hydrophilicity of their corresponding unprotected polyacids.

The dendritic polymers which may be used in the practice of this invention include generally any of the known dendritic architectures including dendrimers, regular dendrons, controlled hyperbranched polymers, dendrigrafts, and random hyperbranched polymers. Dendritic polymers Lire polymers with densely branched structures having a large number of reactive groups. A dendritic polymer includes several layers or generations of repeating units which all contain one or more branch points. Dendritic polymers, including dendrimers and hyperbranched polymers, are prepared by condensation reactions of monomeric units having at least two different types of reactive groups.

Dendrimers are comprised of a plurality of dendrons that emanate from a common core which can be a single atom or a group of atoms. Each dendron generally consists of terminal surface groups, interior branch junctures having branching functionalities greater than or equal to two, and divalent connectors that covalently connect neighboring branching junctures. Dendrons and dendrimers can be prepared by convergent or divergent synthesis. Divergent synthesis of dendrons and dendrimers involves a molecular growth process which occurs through a consecutive series of geometrically progressive step-wise additions of branches upon branches in a radially outward molecular direction to produce an ordered arrangement of layered branch cells, in which each macromolecular includes a core cell, one or more layers of internal cells, and an outer layer of surface cells, wherein each of the cells includes a single branch juncture. The cells can be the same or different in chemical structure and branching functionality. The surface branch cells may contain either chemically reactive or passive functional groups. Chemically reactive surface groups can be used for further extension of dendritic growth or for modification of dendritic molecular surfaces. The chemically passive groups may be used to physically modify dendritic surfaces, such as to adjust the ratio of hydrophobic to hydrophilic terminals. Convergent synthesis of dendrimers and dendrons involves a growth process which begins from what will become the surface of the dendron or dendrimer and progresses radially in a molecular direction toward a focal point or cove.

A third method by which dendrimers and dendrons can be prepared is by using a one-pot synthesis in which dendritic polymers are prepared by a step-growth polymerization reaction of a single type of monomer having a single reactive group of a first type (B) and a plurality (y) of reactive groups of a second type (A), i.e., a B-Ay type monomer, which is initiated by a core having a plurality (x) of the A type reactive groups, wherein A groups can react with B groups, but not with other A groups, and B groups cannot react with other B groups. The one-pot synthesis method is simpler and less expensive than the divergent and convergent synthesis methods. However, the one-pot synthesis method lacks reaction control, which leads to more polydispersed products with larger deviations from ideal dendron structure.

Hyperbranched polymers represent a class of dendritic polymers which contain high levels of non-ideal irregular branching arrays as compared with the more nearly perfect regular structure of dendrons and dendrimers. Specifically, hyperbranched polymers contain a relatively high number of irregular branching arrays in which not every repeat unit contains a branch juncture. Consequently, hyperbranched polymers may be viewed as intermediate between randomly branched polymers and regular dendrons and dendrimers, yet dendritic, because of their relatively high branch-juncture content per individual macromolecule.

Both in the convergent construction of dendrimers and in the dendrimerization or dendron-coating of materials and surfaces, dendrons of different size and surface coatings have been shown to play key role. For example, the 1→3 C-branched monomer, di-tert-butyl 4-[2-tert-butoxycarbonyl)ethyl]-4-aminoheptanedioate, "Behera's Amine", was developed and its use in the divergent synthesis of a family of amide-connected dendrimers was demonstrated. The facile conversion of Behera's amine to a corresponding isocyanate has further expanded its utilitarian uses. There was further convergently created the related second and third generation dendrons. These 1→3 C-branched monomers are easily attached to a particular core, have a specific molecular structure and are easily transformed to the corresponding acidic surface.

The convergent route used to generate the higher generation dendrons used the typical amidation coupling reaction in which a combination of dicyclohexylcarbodiimide (DCC) and 1-hydroxy-benzotriazole (1-HOBT) in dimethylformamide (DMF) were used as reagents of choice. In general, the yields were generally moderate and the desired products were difficult to purify given the formation of dicyclohexyl urea (DCU), which is highly insoluble in most common organic solvents.

It would be advantageous to provide a route of synthesis requiring fewer steps than the aforementioned methods. More particularly, it would be advantageous to provide a route of synthesis that generates a high-yield of pure 1→3 C-branched dendrimers without the use of DCC and 1-HOBT and devoid of DCU unless it is present as a contaminant in a separate reactant used in the route of synthesis.

SUMMARY OF THE INVENTION

In accordance with the present invention, there is provided a method of preparing a dendrimer. In particular, 1→3 C-branched dendrimers can be prepared by reacting an amine with at least acryloyl chloride to form a N-substituted amide. The N-substituted amide is reacted with at least nitromethane to form a second amide, and reacting the N-substituted amide and the second amide at a predetermined ratio to form a predendron. The predendron is hydrogenated in the presence of a catalyst to form an amine dendron and reacting the amine dendron with at least an amount of triphosgene to form an isocyanate dendron.

The present invention further provides 1→3 C-branched dendrimers by reacting second amide with at least an amount of acryloyl chloride to form a third amide. The third amide is reacted with at least an amount of nitromethane to form a third generation predendron, and hydrogenating the predendron in the presence of a catalyst to form a third generation dendron and reacting the third generation dendron with at least an amount of triphosgene to form a third generation isocyanate dendron.

The present invention further provides a dendrimer having a plurality of dendrons emanating from a common core and is devoid of dicyclohexyl urea as a by-product unless the dicyclohexyl urea is present as a contaminant.

DETAILED DESCRIPTION OF THE INVENTION

Generally, the present invention provides a novel method of preparing 1→3 C-branched dendritic materials. More specifically, the present invention provides a novel method of preparing second and third generation dendrons from a convergent synthesis route without using DCC and 1-HOBT as standard reagents used in typical amidation coupling reactions, thereby yielding a final product that is devoid of dicyclohexyl urea as a by-product, unless it is present as a contaminant.

Figure 1:
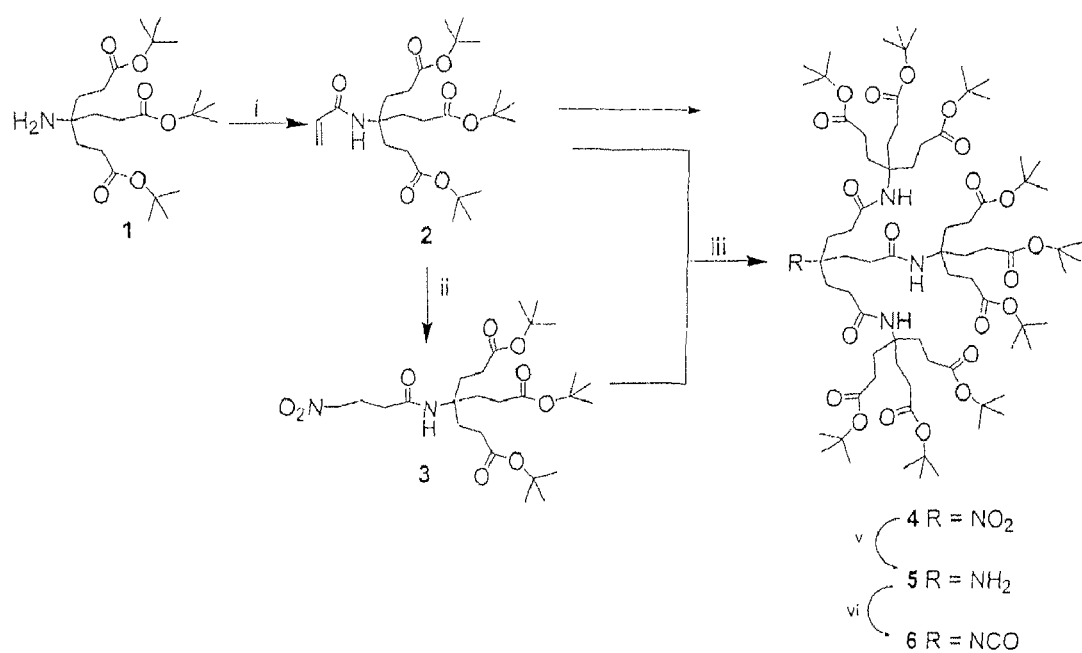
FIG. 1 is a schematic representation of a synthesis for producing intermediates for preparing dendrons in accordance with the present invention.
Figure 3:
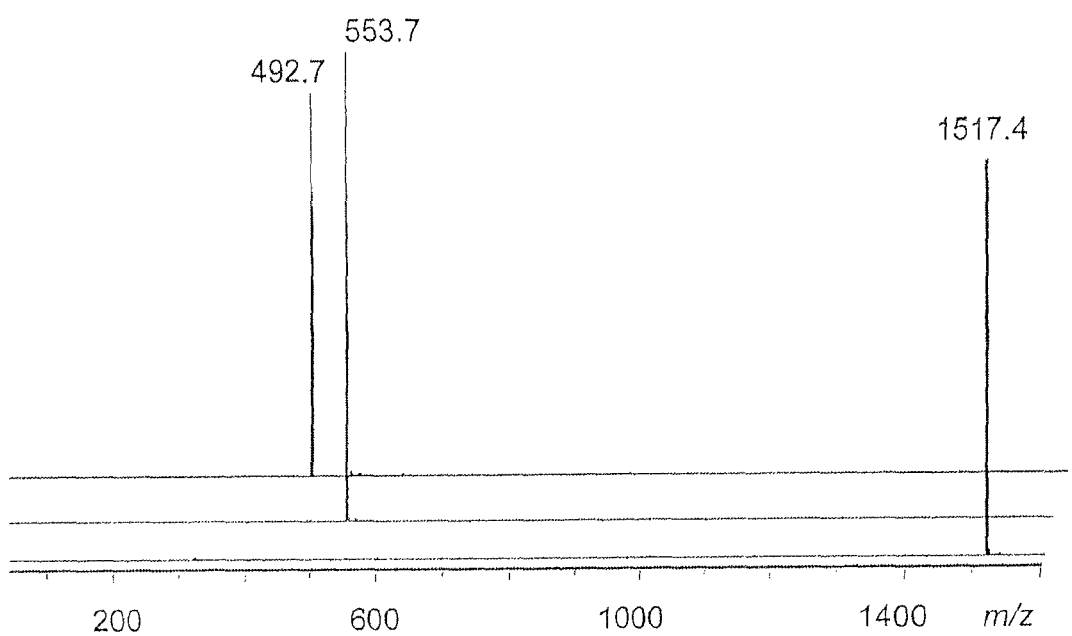
FIG. 3 is a ESI-MS spectrum of compounds 2, 3 and 7 as shown in FIGS. 1 and 2.

As seen in FIG. 1, the novel route of synthesizing the 1→3 C-branched dendrons begins with treating Behera's amine 1, previously synthesized (>95% overall) in two-steps[1,3] from $MeNO_2$ and tert-butyl acrylate followed by catalytic reduction, with one equivalent of acryloyl chloride in the presence of triethylamine ($Et_3N$) in $CH_2Cl_2$ to give (96%) the N-substituted amide 2. The N-substituted amide 2 was confirmed by the new peaks ($^{13}C$ NMR) assigned to the new amido group at 164.7 ppm (C=O), as well as the expected chemical shift change for the $N^{4o}$ C. peak (52.0 to 57.4 ppm) upon amidation and its ESI-MS, as seen in FIG. 3, further confirmed the assignment by a peak at m/z 492.2 [M+Na$^+$]. Michael addition of $MeNO_2$ to 2 in the presence of trimethylglycine (TMG) afforded (85%) the amide 3, whose structure was supported ($^{13}C$ NMR) by the appearance of a new resonance (74.5 ppm) for the primary $CH_2NO_2$ group as well as the absence of olefinic signals. Again the use of Michael-type reaction conditions with two equivalents of acryl amide 2 and reagent 3 in the presence of TMG in tetrahydrofuran (THF) at 50° C. for 15 h gave 91%) the desired second-generation nitro predendron 4. The notable chemical shift for the resonance assigned to the $CR_2NO_2$ group from 74.5 to 92.1 ppm supports the coupling procedure. Different acryl amide monomers derived from other branched monomers can also be attached to afford easy access to heterogeneously functionalized higher generation dendrons. A one-step treatment of $MeNO_2$ with three equivalents of the acryl amide 2 in the presence of TMG in THF afforded a near quantitative yield of the predendron 4. Reduction of the focal nitro group with Raney-Ni[31] in absolute EtOH at 40° C. smoothly afforded (>95%) the desired amino dendron 5, as evidenced by the up-field chemical shift ($^{13}C$ NMR) of the signal assigned to the $H_2NC$ from 92.1 to 52.3 ppm; this sample is identical in all respects to a sample prepared by the convergent procedure.

Figure 2:
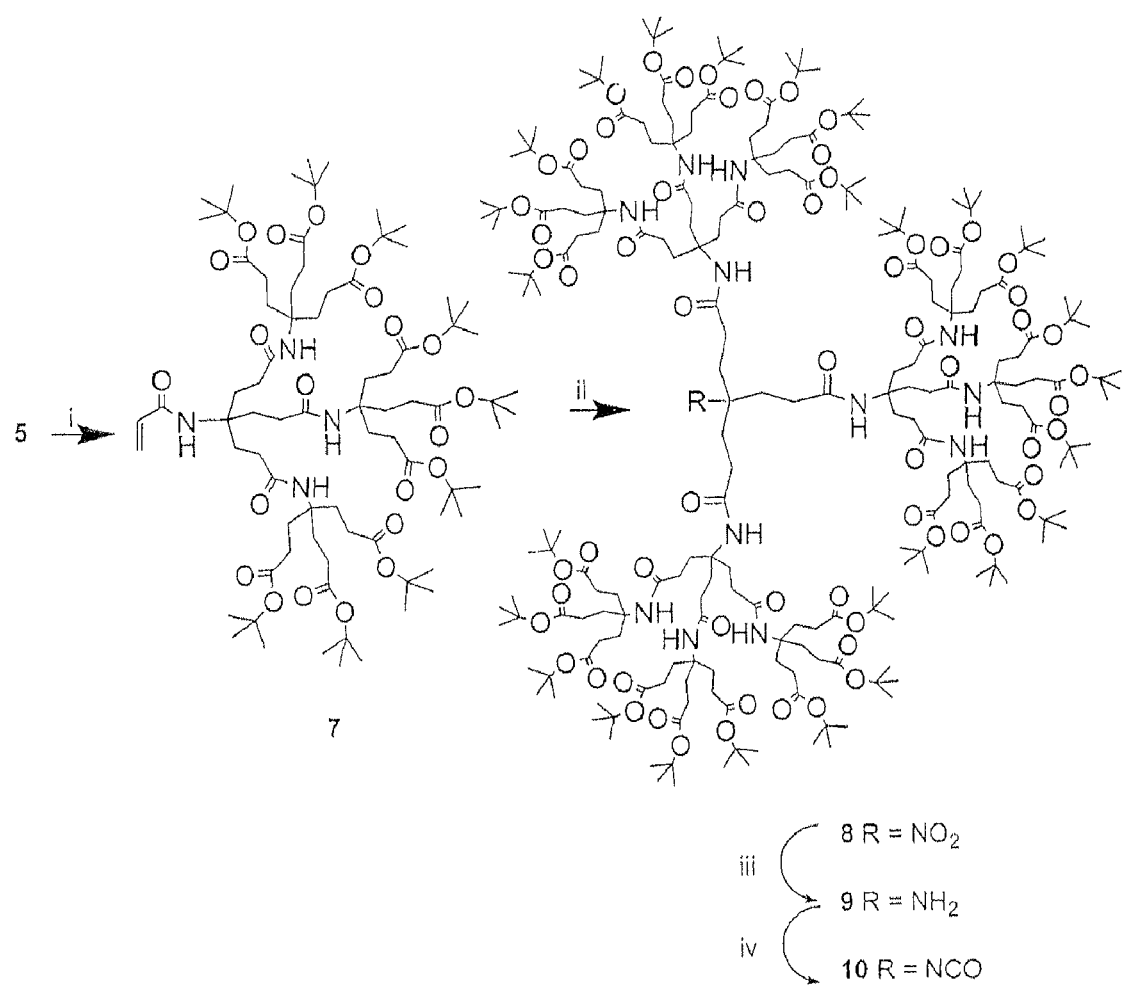
FIG. 2 is a schematic representation of a synthesis for producing a further generations of dendrons in accordance with the present invention.

As seen in FIG. 2, Synthesis of $2^{nd}$ generation acryl amide 7 was achieved (93%) by the treatment of acryloyl chloride with $2^{nd}$ generation amine 5 in the presence of $Et_3N$ in dry dichloromethane (DCM). The presence of three different carbonyl groups in its $^{13}C$ NMR spectrum and the molecular peak at m/z 1516.2 [M+Na$^+$] in the ESI-MS, as seen in FIG. 3, support the amidation. Subjecting the $2^{nd}$ generation acryl amide 7 and $MeNO_2$ in the presence of TMG in refluxing THF for 24 h lead (82%) to the third generation predendron 8, which was structurally established by the new signal (92.7 ppm) for $O_2N^{4o}$ C. and the molecular peak (matrix assisted laser desorption ionization time-of-flight or MALDI-TOF) at m/z 4567.2 [M+Na$^+$]. Reduction of the nitro moiety of 8 with Raney Ni catalyst in absolute ethanol at 50° C. afforded (85%) the $3^{rd}$ generation amine dendron 9, which was supported by the chemical shift ($^{13}C$ NMR) for the quaternary carbon from $O_2NQ$ 92.7 to 52.3 ($H_2NC$) ppm and the molecular ion peak (MALDI-TOF) at m/z 4537.4 [M+Na$^+$].

Subsequent treatment of amines 5 and 9 with 0.5 equiv. of triphosgene in the presence of $Et_3N$ in dry THF gave the desired isocyanates 6 and 10 respectively, whose structures were confirmed by their $^{13}C$ NMR spectra, which showed a chemical shift for the OCNC signal from 52.3 and 52.4 ppm to 62.3 and 59.9 ppm, respectively, as well as the presence of a new peak at 122.4 and 125.5 ppm for the NCO group. In addition, the IR spectra of both showed an isocyanate peak at 2261 or 2256 cm$^{-1}$ and signals (ESI-MS and MALDI-TOF) at m/z 1512.1 [M+Na$^+$] (6: calculated m/z 1510.9 [M+Na$^+$]) and m/z 4562.2 [M+Na$^+$] (10: calculated m/z 4561.9 [M+Na$^+$]) further characterized the transformation of the amine group.

The following working examples are given to illustrate the disclosed 1→3 C-branched dendrimers. All parts and percentages are by weight unless otherwise indicated.

Example 1

Synthesis of Di-tert-butyl 4-Acryloylamino-4-(2-tert-butoxycarbonylethyl)-heptanedioate (2)

To a stirred solution of Behera's amine (1; 4.6 g, 11 mmol) and $Et_3N$ (3.1 mL, 22 mmol) in dry DCM at 0° C., acryloyl chloride (1 g, 11 mmol) was added. After 2 h at 25° C., the reaction mixture was washed with water then saturated brine, The organic solution was dried ($MgSO_4$), filtered, and concentrated in vacuo to give a crude solid, which was chromatographed ($SiO_2$) eluting with a 1.0% EtOAc in $CHCl_3$ mixture to afford (96%) amide 3, as a white solid: 5.3 g; mp 144-145° C.; $^1H$ NMR δ 1.44 (s, 27H, $CH_3$), 2.04 (t, 6H, J=7.5 Hz, $CH_2CH_2CO$), 2.26 (t, 6H, J=7.5 Hz, $CH_2CO$), 5.59 (dd, J=12, 1.5 Hz, 1H, $CH_2$=CH), 6.03 (dd, J=19.0, 10.0 Hz, 1H, $CH_2$=CH), 6.20 (s, 1H, NH), 6.22 (dd, J=18.0, 1.5 Hz, 1H, $CH_2$=CH); $^{13}C$ NMR δ 27.9 ($CH_3$), 29.6 ($CH_2$=$CO_2$), 29.9 ($CH_2CH_2CO_2$), 57.4 (NHC), 80.3 ($CMe_3$), 125.5 ($CH_2$=CH), 131.7 ($CH_2$=CH), 164.7 (CONH), 172.7 ($CO_2$); IR 3290, 1710, 1654, 1622 cm$^{-1}$; MS ESI: 492.2, (calculated) 492.3 [M+Na$^+$]. Analysis —($C_{25}H_{43}NO_7$) Found: C, 63.68; H, 9.30; N, 2.84. Calculated C, 63.94; H, 9.23; N, 2.98.

Example 2

Synthesis of Di-tert-butyl 4-(2-tert-Butoxycarbonyl-ethyl)-4-(4-nitrobuta-2,3-dienoylamino)heptanedioate (3)

To a stirred solution of acryl amide 2 (2 g 4.2 mmol) in a $MeNO_2/CHCl_3$ mixture (1:1; 100 mL), TMG 200 μL) was added and maintained at 25° C. for 24 h. The mixture was then concentrated in vacuo to give a crude solid, which was dissolved in $CHCl_3$ then sequentially washed with dilute aqueous HCl, water, and saturated brine. The organic solution was dried ($Na_2SO_4$), filtered, and concentrated in vacuo to give a crude oil, which was column chromatographed ($SiO_2$) eluting with 25% ethyl acetate (EtOAc) in hexane to give (93%) amide 3, as a white solid: 2.1 g; mp 140-141° C.; $^1H$ NMR δ 1.45 (s, 27H, $CH_3$), 1.99 (t, 6H, J=7.5 Hz, $CH_2CH_2CO$), 2.24 (t, 6H, J=7.5 Hz, $CH_2CO$), 2.26 (m, 4H, $CH_2CH_2CO$), 4.47 (t, 2H, J=6 Hz, $O_2NCH_2$), 6.19 (s, 1H, N); $^{13}C$ NMR δ 22.8 ($CH_2CO$), 27.7 ($CH_3$), 29.6 ($CH_2CO$), 29.8 ($CH_2CH_2CO$), 32.4 ($O_2NCH_2CH_2$), 57.3 (NHC), 74.5 ($O_2NCH_2$), 80.2 ($CMe_3$), 170.1 (CONH), 172.4 ($CO_2$); IR 3300, 1710, 1670, 1552 $cm^{-1}$; MS ESI; 553.3, Calculated 553.3 [M+Na$^+$]. Analysis ($C_{26}H_{46}N_2O_9$) Found C, 57.94; H, 8.66; N, 5.20. Calculated C, 58.85; H, 8.74; N, 5.28.

Example 3

Synthesis of $2^{nd}$ Generation Nitro Predendron (4)

Acryl amide 2 (1.9 g, 4.0 mmol) and TMG (250 μL) were added to a stirred solution of amide 3 (1 g, 1.9 mmol) in dry THF (100 mL). After the mixture was stirred for 15 h at 50° C., the solution was concentrated in vacuo to give a solid residue, which was dissolved in $CHCl_3$ and then sequentially washed with dilute HCl, water, and saturated brine. The organic solution was dried ($Na_2SO_4$), filtered, and reduced in vacuo to give a oil, which was column chromatographed ($SiO_2$) eluting with EtOAc/hexane (1:2) mixture to give (95%) 4, as a white solid: 2.5 g; m.p. 157° C.; $^1H$ NMR δ 1.44 (s, 81H, $CH_3$), 1.93 (t, 18H, $CH_2Cl_2CO_2$, 17.0 Hz) 2.12 (t, 30H, $CH_2CH_2CO_2$, $CH_2CH_2CONH$, J=7.0 Hz), 6.20 (s, 3H, CONH); $^{13}C$ NMR δ 28.2 ($CH_3$), 29.8, 29.9 ($CH_2CH_2CO_2$), 31.4 ($CH_2CH_2CONH$), 57.7 (CONHC), 80.8 ($CMe_3$), 92.6 ($O_2NC$), 170.6 (CONH), 172.9 ($CO_2$); IR: 3360, 2979, 1731, 1681 $cm^{-1}$; ESI-MS: m/z 1493.4 [M+Na$^+$]; calc. m/z=1492.9 [M+Na$^+$].

Example 4

$2^{nd}$ Generation Amine Dendron (5)

The amine dendron 5 was generated by a catalytic hydrogenation of the predendron 4 with T-1 Raney nickel in absolute EtOH at 65 psi at 50° C. for 15 h. The pyrophoric solution was cautiously filtered through celite, then the filtrate was concentrated in vacuo to give (>95%) pure amine dendron 5: m.p. 193-194° C.; $^1H$ NMR δ 1.51 (s, 81H, $CH_3$), 2.01 (t, 18H, $CH_2CH_2CO_2$, J=7.0 Hz), 2.12 (t, 30H, $CH_2CH_2CO_2$, $CH_2CH_2CONH$, J=7.0 Hz), 6.22 (s, 3H, CONH), 6.31 (s, 2H, $NH_2$); $^{13}C$ NMR δ 28.2 ($CH_3$), 29.8, 29.9 ($CH_2CH_2CO_2$), 31.4 ($CH_2CH_2$, CONH), 57.7 (CONHC), 52.3 ($H_2NC$), 80.8 ($CMe_3$), 170.6 (CONH), 172.9 ($CO_2$), 172.9 ($CO_2$); IR 3360, 2979, 1731, 1681 $cm^{-1}$; ESI-MS: m/z=1493.4 [M+Na$^+$]; calculated m/z 1492.9 [M+Na$^+$].

Example 5

Synthesis of $2^{nd}$ Generation Isocyanate (6)

The $2^{nd}$ generation amine 5 (0.5 g, 0.34 mmol) was dissolved in dry THF (20 ml), $Et_3N$ (50 μl, 0.68 mmol) was added to the same flask under nitrogen atmosphere, then it was cooled to 0° C. A solution of triphosgene (51 mg, 0.17 mmol) in THF (5 ml) was added drop-wise at 0° C. over 20 min. After the addition was completed, the stirred reaction mixture was allowed to warm to 25° C., after 3 h, the white precipitate was filtered and filtrate was concentrated in vacuo to give a residue, which was dissolved in $CHCl_3$ washed with water, dried ($MgSO_4$), and then concentrated in vacuo to give a solid, which column chromatographed ($SiO_2$) eluting with EtOAc/hexane (1:3) to afford 0.71 g, 70% the second generation isocyanate 6, as a foam solid: $^1H$ NMR: δ 1.49 (s, 81H, $CH_3$), 2.0 (br m, 18H, $CH_2CH_2CO_2$), 2.12 (br m, 30H, $CH_2CH_2COO$, $CH_2CH_2CONH$), 6.33 (s, 3H, CONH); $^{13}C$ NMR: δ 27.5 ($CH_3$), 29.3, 29.6 ($CH_2CH_2CO_2$), 31.1, 31.7 ($CH_2CH_2CONH$), 57.4 (CONHC), 62.3 (OCNC), 80.2 ($CMe_3$), 122.4 (NCO, 171.2 (CONH), 172.9 ($CO_2$); IR: 3363, 2978, 2936, 2260 (N CO, 1730 (ester C=O), 1680 (amide C=O) $cm^-$; ESI-MS: m/z=1512.1 [M+Na$^+$]; calc. m/z=1510.9 [M+Na$^+$].

Example 6

Synthesis of Amide (7)

To a stirred solution of $2^{nd}$ generation amine 5 (5 g, 3.5 mmol) and $Et_3N$ (1.0 mL, 9.8 mmol) in anhydrous THF (50 mL), was added acroyl chloride (310 mg, 3.5 mmol) in THF (20 mL) under nitrogen atmosphere at 0° C., then maintained for 3 hr at 25° C. The reaction mixture was filtered and concentrated in vacuo to give the crude product, which was dissolved in $CHCl_3$ and washed with saturated brine solution, followed by water, dried ($MgSO_4$), filtered and concentrated in vacuo to get a foam solid, which was chromatographed ($SiO_2$) eluding with EtOAc/hexane (1:2) to afford (93%) of 7, as a white solid: 4.8 g; $^1H$ NMR δ 1.44 (s, 81H, $CH_3$), 1.95 (t, 18H, J=6.9 Hz), 2.04 (br m, 12H), 2.20 (t, 18H, J=6.9 Hz), 5.54 (dd, J=12, 1.5 Hz, 1H, $CH_2$=CH), 6.06 (dd, J=19.0, 10.0 Hz, 1H, $CH_2$=CH), 6.11 (br, 2H, NH), 6.21 (dd, J=18.0, 1.5 Hz, 1H, $CH_2$=CH); $^{13}C$ NMR δ 27.9 ($CH_3$), 29.7, 29.9 ($CH_2CH_2CO_2$), 31.6, 32.0 ($CH_2CH_2CONH$), 57.3 (CONHC), 57.7 (HNC), 80.4 ($CMe_3$), 125.4, ($CH_2$=CH), 132.1 ($CH_2$=CH), 165.5 (CONH), 172.5 (CONH), 172.9 ($CO_2$); IR 3280, 1710 (ester C=O), 1654 (amide C=O), 1622 $cm^{-1}$; ESI-MS: m/z=1516.2 [M+Na$^+$]; calculated m/z=1515.6 [M+Na$^+$]. Analysis ($C_{79}H_{136}N_4O_{22}$) Found: C, 63.04; H, 9.13; N, 3.74. Calculated—C, 63.51; H, 9.18; N, 3.75.

Example 7

Synthesis of $3^{rd}$ Generation Predendron (8)

Nitro methane (40 mg, 0.65 mmol) and TMG (100 μl) were dissolved in anhydrous THF, $2^{nd}$ generation acryl amide 7 (2.9 g, 1.9 mmol) in THF was added. The mixture was refluxed tinder nitrogen for 12 h, cooled, and concentrated in vacuo to give the crude product. The residue was dissolved in $CHCl_3$, washed with water, dried ($MgSO_4$), filtered, and concentrated in vacuo to give a solid, which was column chromatographed ($SiO_2$) eluting with EtOAc/hexane (1:2) to afford (82%) $3^{rd}$ generation predendron 8, as a white solid:

800 mg; $^1$H NMR δ 1.42 (s, 243H, CH$_3$), 1.93 (br m, 78H, CH$_2$CH$_2$CO$_2$, CH$_2$CH$_2$CONH), 2.12 (br m, 78H, CH$_2$CO$_2$, CH$_2$CONH), 6.19 (s, 12H, CONH); $^{13}$C NMR δ 27.3 (CH$_3$), 29.2 (CH$_2$CH$_2$CO$_2$), 33.6 (CH$_2$CH$_2$CONH), 56.7 (CONHCCH$_2$CH$_2$CO$_2$), 57.5 (CONHC), 80.1 (CMe$_3$), 92.7 (O$_2$NC), 170.5 (CONH), 170.9 (CONH), 172.5 (CO$_2$); IR: 3358, 2978, 2936 1730 (ester C=O), 1654 (amide C=O) cm$^{-1}$; MALDI-TOF MS: m/z=4567.2 [M+Na$^+$]; calculated m/z 4565.8 [M+Na$^+$].

Example 8

3$^{rd}$ Generation Dendron (9)

The predendron 8 (1 g, 0.22 mmol) was dissolved in absolute EtOH (50 ml) and T-1 Raney Ni, hydrogenated at 65 psi at 50° C. for 24 h. The solution was cautiously (pyrophoric) filtered through celite. The solvent was concentrated in vacuo to give a crude compound, which was purified oil column (SiO$_2$) eluding with EtOAc to give (720 mg, 73%) 9, as a white foam solid: $^1$H NMR: δ 1.22 (s, 243H, CH$_3$), 1.77 (br m, 78H, CH$_2$CH$_2$CH$_2$CO$_2$, CH$_2$CH$_2$CONH), 2.00 (br m, 78H, CH$_2$CH$_2$CO$_2$, CH$_2$CH$_2$CONH), 6.14 (s, 12H, CONH); $^{13}$C NMR: δ 27.6 (CH$_3$), 29.5 (CH$_2$CH$_2$CO$_2$), 31.3 (CH$_2$CH$_2$CONH), 52.4 (H$_2$NC), 57.0 (CONHCCH$_2$CH$_2$CO$_2$), 57.5 (CONHC), 80.1 (CMe$_3$), 172.3 (CONH), 172.9 (CO$_2$); IR: 3361, 3334, 2978, 2934, 1730 (ester C=O), 1653 (amide C=O) cm$^{-1}$; MALDI-TOF MS: m/z=4537.3 [M+Na$^+$]; calculated m/z=4534.9 [M+Na$^+$].

Example 9

Synthesis of 3$^{rd}$ Generation Isocyanate (10)

The synthesis of isocyanate 10 followed that of 6 in which the crude reaction mixture was chromatographed (SiO$_2$) eluting with EtOAc/hexane (1:1) to give (57%) the pure isocyanate 10. $^1$H NMR: δ 1.24 (s, 243H, CH$_3$), 1.75 (br m, 78H, CH$_2$CH$_2$CO$_2$, CH$_2$CH$_2$CONH), 2.01 (br m, 78H, CH$_2$CH$_2$CO$_2$, CH$_2$CH$_2$CONH), 6.21 (s, 12H, CONH); $^{13}$C NMR: δ 28.0 (CH$_3$), 29.6 (CH$_2$CH$_2$CO$_2$), 31.5 (CH$_2$CH$_2$CONH), 57.3 (CONHCCH$_2$CH$_2$CO$_2$), 57.7 (CONHC), 59.9 (OCNC), 80.2 (CMe$_3$), 125.5 (OCN), 171.9 (CONH), 172.8 (CO$_2$); IR: 3324, 2978, 2933, 2256 (O=C=N), 1731 (ester C=O), 1655 (amide C=O) cm$^{-1}$; MALDI-TOF MS: m/z=4565.2 [M+Na$^+$]; calc. m/z=4561.9 [M+Na$^+$].

Melting point data were obtained in capillary tubes with an Electrothermal 9100 melting point apparatus and are uncorrected. All of chemicals were purchased from Aldrich Co. except for Behera's amine. THF was dried by refluxing over benzophenone/Na under nitrogen. Dichloromethane was dried over CaH$_2$. All other commercially available solvents were used without further purification. Column chromatography was conducted using silica gel (60-200 mesh) from Fisher Scientific with the stipulated solvent mixture. $^1$H and $^{13}$C NMR spectra were obtained in CDCl$_3$, except where noted, and are recorded at 250 and 52 MHz, respectively. Infrared spectra (IR) were obtained (KBr pellet, unless otherwise noted) and recorded on In ATI Mattson Genesis Series FTIR spectrometer. Mass spectral data were obtained using an Esquire electron ionization mass spectrometer (ESI) and are reported as: (assignment, relative intensity); ESI samples were typically prepared in MeOH/H$_2$O/TFA (70:30:01) for positive ion mode or Me$_2$CHOH/H$_2$O/NH$_3$ (70:30:1) for negative ion mode and MALDI-TOF mass spectrometer.

The invention has been described in an illustrative manner, and it is to be understood that the terminology which has been used is intended to be in the nature of words of description rather than of limitation.

To illustrate the invention, it is shown and described with respect to a specific embodiment. This is not intended as a limitation, and other modifications or variations in the specific form shown and described will be apparent to those skilled in the art.

What is claimed is:

1. A method of preparing a 1→3 C-branched dendrimer, the method comprising the steps of:
   reacting an amine with at least acryloyl chloride to form a N-substituted amide;
   reacting the N-substituted amide with at least nitromethane to form a second amide;
   reacting the N-substituted amide and the second amide at a predetermined ratio to form a predendron;
   hydrogenating the predendron in the presence of a catalyst to form an amine dendron; and
   reacting the amine dendron with at least an amount of triphosgene to form an isocyanate dendron.

2. The method of claim 1 further comprising the steps of:
   reacting second amide with at least an amount of acryloyl chloride to form a third amide;
   reacting the third amide with at least an amount of nitromethane to form a third generation predendron;
   hydrogenating the predendron in the presence of a catalyst to form a third generation dendron; and
   reacting the third generation dendron with at least an amount of triphosgene to form a third generation isocyanate dendron.

3. The method of claim 1, wherein the predendron is a second generation predendron.

4. The method of claim 1, wherein the catalyst is a Raney-Nickel catalyst.

5. The method of claim 1, wherein the amine dendron is a second generation dendron.

6. The method of claim 1, wherein the third amide is a second generation acryl amide.

7. The method of claim 1, wherein the predetermined ratio of the N-substituted amide:second amide is approximately 2:1.

* * * * *